United States Patent
Weider et al.

(10) Patent No.: US 9,382,593 B2
(45) Date of Patent: *Jul. 5, 2016

(54) CONTINUOUS OR SEMI-CONTINUOUS PROCESS FOR TREATING BIOMASS TO PRODUCE MATERIALS USEFUL FOR BIOFUELS

(71) Applicant: SHELL OIL COMPANY, Houston, TX (US)

(72) Inventors: Paul Richard Weider, Houston, TX (US); Robert Lawrence Blackbourn, Houston, TX (US); David Matthew Brown, Houston, TX (US)

(73) Assignee: Shell Oil Company, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/888,412

(22) Filed: May 7, 2013

(65) Prior Publication Data

US 2013/0295629 A1    Nov. 7, 2013

Related U.S. Application Data

(60) Provisional application No. 61/643,633, filed on May 7, 2012.

(51) Int. Cl.

| | |
|---|---|
| *C13K 13/00* | (2006.01) |
| *C12P 19/02* | (2006.01) |
| *C12P 19/14* | (2006.01) |
| *C13K 1/02* | (2006.01) |

(52) U.S. Cl.
CPC ............... *C13K 13/00* (2013.01); *C12P 19/02* (2013.01); *C12P 19/14* (2013.01); *C13K 1/02* (2013.01); *C12P 2201/00* (2013.01); *C12P 2203/00* (2013.01); *Y02E 50/16* (2013.01)

(58) Field of Classification Search
CPC ...... C13K 13/00; C13K 1/02; C12P 2201/00; C12P 2203/00; C12P 19/14; C12P 19/02
See application file for complete search history.

(56) References Cited

U.S. PATENT DOCUMENTS

| | | | |
|---|---|---|---|
| 2,308,564 | A | 1/1943 | McKee |
| 3,248,278 | A | 4/1966 | Wilson |
| 3,549,319 | A | 12/1970 | Wilson et al. |
| 3,821,355 | A | 6/1974 | Bandyopadhyay et al. |
| 4,113,842 | A | 9/1978 | McCullough et al. |
| 4,238,459 | A | 12/1980 | Phillips, Jr. et al. |
| 4,306,101 | A | 12/1981 | Slaugh et al. |

(Continued)

FOREIGN PATENT DOCUMENTS

| | | |
|---|---|---|
| EP | 1727890 | 5/2008 |
| WO | 9513362 | 5/1995 |

(Continued)

OTHER PUBLICATIONS

Galbe, M. et al.; "A review of the production of ethanol from softwood"; Appl Microbiol Biotechnol; vol. 59; pp. 618-628; 2002.

(Continued)

*Primary Examiner* — Karen Cochrane Carlson
*Assistant Examiner* — Jennifer M. H. Tichy

(57) ABSTRACT

Fermentable sugar useful for the production of biofuels is produced from biomass in a continuous or semi-continuous manner by providing pumpable biomass.

26 Claims, 1 Drawing Sheet

(56) References Cited

U.S. PATENT DOCUMENTS

| | | | |
|---|---|---|---|
| 4,316,008 | A | 2/1982 | Willis et al. |
| 4,395,356 | A | 7/1983 | Slaugh et al. |
| 4,396,761 | A | 8/1983 | Willis et al. |
| 4,409,032 | A | 10/1983 | Paszner et al. |
| 4,461,648 | A | 7/1984 | Foody |
| 4,612,286 | A | 9/1986 | Sherman et al. |
| 4,669,545 | A | 6/1987 | Slaugh |
| 5,536,325 | A | 7/1996 | Brink |
| 5,789,210 | A | 8/1998 | Ho et al. |
| 5,820,687 | A | 10/1998 | Farone et al. |
| 6,475,768 | B1 | 11/2002 | Otero et al. |
| 7,741,084 | B2 | 6/2010 | Viitanen et al. |
| 7,741,119 | B2 | 6/2010 | Viitanen et al. |
| 7,781,191 | B2 | 8/2010 | Dunson, Jr. et al. |
| 2003/0162271 | A1 | 8/2003 | Zhang et al. |
| 2008/0216391 | A1 | 9/2008 | Cortright et al. |
| 2009/0061490 | A1 | 3/2009 | Edwards et al. |
| 2010/0184151 | A1 | 7/2010 | Tolan et al. |
| 2011/0154721 | A1 | 6/2011 | Chheda et al. |
| 2011/0282115 | A1 | 11/2011 | Chheda et al. |
| 2012/0122152 | A1 | 5/2012 | Blackbourn et al. |
| 2013/0144078 | A1* | 6/2013 | Wang et al. .................. 554/187 |
| 2013/0157333 | A1* | 6/2013 | Tetarenko et al. ............ 435/162 |
| 2013/0196400 | A1* | 8/2013 | Weider et al. ................ 435/161 |
| 2013/0309727 | A1* | 11/2013 | Hamilton et al. ............... 435/99 |
| 2014/0024093 | A1* | 1/2014 | Blackbourn et al. .......... 435/158 |

FOREIGN PATENT DOCUMENTS

| | | |
|---|---|---|
| WO | 9742307 | 11/1997 |
| WO | 0202826 | 1/2002 |
| WO | 2006007691 | 1/2006 |
| WO | 2006096130 | 9/2006 |
| WO | 2007009463 | 1/2007 |
| WO | 2007028811 | 3/2007 |
| WO | 2007136762 | 11/2007 |
| WO | 2008119082 | 10/2008 |
| WO | 2009109631 | 9/2009 |
| WO | 2010026572 | 3/2010 |
| WO | 2010029568 | 3/2010 |
| WO | 20100046051 | 4/2010 |
| WO | 2010071805 | 6/2010 |
| WO | 2012061596 | 5/2012 |
| WO | 2013082141 | 6/2013 |

OTHER PUBLICATIONS

Ong Lim Koon; "Conversion of Lignocellulosic Biomass to Fuel Ethanol—a Brief Review"; The Planter; vol. 80 No. 941; pp. 517-524; Aug. 2004.

Moller, Dr. Ralf; "Cell Wall Saccharification"; Outputs from the EPOBIO project; pp. 1-69; 2006.

Holtzapple, M.T., et al.; "The ammonia freeze explosion (AFEX) process-a practical lignocellulose pretreatment"; Applied Biochemistry and Biotechnology; vol. 28/29; pp. 59-74; 1991.

Kumar, P. et al.; "Methods for Pretreatment of Lignocellulosic Biomass for Efficient Hydroloysis and Biofuel Production" ; Ind. Eng. Chem. Res.; vol. 48; pp. 3713-3729; 2009.

Lavarak, B.P., et al: The acid hydrolysis of sugarcane bagasse hemicelluloses to product xylose, arabinose, glucose and other product; Biomass and Bioenergy; vol. 23; pp. 367-380; 2002.

Brown, Robert; "Fast Pyrolysis and Bio-Oil Upgrading, Biomass-to-Diesel Workshop"; Pacific Northwest National Laboratory; pp. 1-46 ; Sep. 5-6, 2006.

Mosier, N., et al: "Features of promising technologies for pretreatment of lignocellulosic biomass"; Bioresource Technology; vol. 96; pp. 673-686; 2005.

Humbird, D., et al.; "Economic Impact of Total Solids Loading on Enzymatic Hydrolysis of Dilute Acid Pretreated Corn Stover"; Biotechnol. Prog., vol. 26, No. 5, pp. 1245-1251; May 26, 2010.

International Search Report dated Mar. 26, 2012 for related application PCT/US2011/059140; 5 pages.

International Search Report dated Jul. 19, 2013 for PCT/US2013/039843 a counterpart application; 5 pages.

Balat, M. et al.; "Recent trends in global production and utilization of bio-ethanol fuels"; Applied Energy; vol. 86; pp. 2273-2282; 2009.

* cited by examiner

CONTINUOUS OR SEMI-CONTINUOUS PROCESS FOR TREATING BIOMASS TO PRODUCE MATERIALS USEFUL FOR BIOFUELS

The present application claims the benefit of U.S. Patent Application No. 61/643,663, filed May 7, 2012 the entire disclosure of which is hereby incorporated by reference.

FIELD OF THE INVENTION

The invention relates to a process for treating biomass, and more specifically to a pretreatment of biomass for the production of sugars from materials containing polysaccharides and compositions, for use in biofuel or other high value products.

BACKGROUND OF THE INVENTION

Lignocellulosic biomass is viewed as an abundant renewable resource for fuels and chemicals due to the presence of sugars in the cell walls of plants. More than 50% of the organic carbon on the earth's surface is contained in plants. This lignocellulosic biomass is comprised of hemicelluloses, cellulose and smaller portions of lignin and protein. These structural components are comprised primarily of pentose and hexose sugars monomers. Cellulose is a polymer comprised mostly of condensation polymerized glucose and hemicellulose is a precursor to pentose sugars, mostly xylose. These sugars can easily be converted into fuels and valuable components, provided they can be liberated from the cell walls and polymers that contain them. However, plant cell walls have evolved considerable resistance to microbial, mechanical or chemical breakdown to yield component sugars. In order to overcome recalcitrance ground biomass is altered by a chemical process known as pretreatment. The aim of the pretreatment is to hydrolyze the hemicellulose, break down the protective lignin structure and disrupt the crystalline structure of cellulose. All of these steps enhance enzymatic accessibility to the cellulose during the subsequent hydrolysis (saccharification) step.

Pretreatment is viewed as one of the primary cost drivers in lignocellulosic ethanol and as a consequence a number of pretreatment approaches have been investigated on a wide variety of feedstocks types. The Saccharification of the cellulose enzymatically holds promise of greater yields of sugars under milder conditions and is therefore considered by many to be more economically attractive. The recalcitrance of the raw biomass to enzymatic hydrolysis necessitates a pretreatment to enhance the susceptibility of the cellulose to hydrolytic enzymes. A number of pretreatment methods, such as described in Nathan Mosier, Charles Wyman, Bruce Dale, Richard Elander, Y. Y. Lee, Mark Holtzapple, Michael Ladisch 'Features of promising technologies for pretreatment of lignocellulosic biomass" Bioresource Technology 96 (2005) pp.673-686, have been developed to alter the structural and chemical composition of biomass to improve enzymatic conversion. A very recent comparison of "leading pretreatment" technologies was accomplished by the Biomass Refining Consortium for Applied Fundementals and Innovation (CAFI) and reported out in the journal Bioresource Technology in December of 2011. Such methods include treatment with dilute acid steam explosion described in U.S. Pat. No. 4,461,648, hydrothermal pretreatment without the addition of chemicals described in WO 2007/009463 A2, ammonia freeze explosion described in AFEX; Holtzapple, M. T., Jun, J., Ashok, G., Patibandla, S. L., Dale, B. E., 1991, The ammonia freeze explosion (AFEX) process—a practical lignocellulose pretreatment, Applied Biochemistry and Biotechnology 28/29, pp. 59-74, and organosolve extraction described in U.S. Pat. No. 4,409,032. Despite this, pretreatment has been cited as the most expensive process in biomass-to-fuels conversion ("Methods for Pretreatment of Lignocellulosic Biomass for Efficient Hydrolysis and Biofuel Production" Ind. Eng. Chem. Res., 2009, 48(8), 3713-3729.)

One pretreatment that has been extensively explored is a high temperature, dilute-sulfuric acid ($H_2SO_4$) process, which effectively hydrolyzes the hemicellulosic portion of the biomass to soluble sugars and exposes the cellulose so that enzymatic Saccharification is successful. The parameters which can be employed to control the conditions and effectiveness of the pretreatment are time, temperature, and acid loading. These are often combined in a mathematical equation termed the combined severity factor. In general, the higher the acid loading employed, the lower the temperature that can be employed; this comes at a cost of acid and its subsequent neutralization. Conversely, the lower the temperature, the longer the pretreatment process takes; this comes at the cost of volumetric productivity. It is desirable to lower the temperature because pentose sugars readily decompose to form furfurals and other species which represents a yield loss and these compounds are poisons to downstream fermentation. However the use of the higher concentrations of acid required to lower the pretreatment temperatures below that where furfural formation becomes facile (B. P. Lavarack, G. J. Griffin, D. Rodman "The acid hydrolysis of sugarcane bagasse hemicelluloses to product xylose, arabinose, glucose and other products." Biomass and Bioenergy 23 (2002) pp. 367-380) requires sufficient quantities of acid that the recovery of the strong acid is an economic imperitive. If dilute acid streams and higher temperatures are employed the pretreatment reaction produces increased amounts of furfural and the acid passing downstream must be neutralized resulting in inorganic salts which complicates downstream processing and requires more expensive waste water treatment systems.

The amount of water employed in pretreatment further impacts the downstream energy balance and the overall economics of the fuel ethanol process. Further, there has been a recent review article studying the economic impact of total solids loading on enzymatic hydrolysis of pretreated corn stover produced by dilute sulfuric acid pretreatment (Humbird, D., Mohagheghi, A., Dowe, N., Schell D. J. "Economic Impact of Total Solids Loading on Enzymatic Hydrolysis of Dilute Acid Pretreated Corn Stover" Biotechnol. Prog., 2010, Vol. 26, No. 5, 1245-1251. (Published online May 26, 2010). It is thought that in a commercially relevant cellulosic ethanol process at scale, it will be necessary to carry out enzymatic cellulose hydrolysis on the whole pretreated slurry at a higher total solids loading. While it is mentioned in the article that it may be economically necessary, performing enzymatic hydrolysis at a high total solids loading remains challenging with reduced enzymatic yields. This is, in part due to an increase in the toxic impurities generated in the more concentrated pretreatment processes.

SUMMARY OF THE INVENTION

Given the above information it is desirable to provide a biomass pretreatment process to provide high total solids loading for enzymatic cellulose hydrolysis that can provide better enzymatic yields. Further, it is desireable to provide a biomass pretreatment process that can be operated in a continuous or semi-continuous manner rather than batch processes.

In an embodiment of the present invention a continuous or a semi-continuous process for treating biomass comprises:

(a) providing a biomass containing polysaccharides;

(b) contacting the biomass with a solution containing at least one α-hydroxysulfonic acid at a temperature within the range of about 50° C. to about 150° C. and a pressure within the range of 1 barg to about 10 barg to provide a biomass solution, wherein said biomass solution contains in the range of about 1 wt % to about 25 wt % of biomass based on the solution, and thereby hydrolyzing the biomass to produce at least one fermentable sugar containing product;

(c) removing the α-hydroxysulfonic acid in its component form from the product by heating and/or reducing pressure to produce an acid-removed product containing at least one fermentable sugar substantially free of the α-hydroxysulfonic acid;

(d) separating a high solids/liquid mixture from said acid-removed product to form a wet solids stream containing at least 12 wt % undissolved solids based on wet solids stream, and a bulk liquid stream containing at least one fermentable sugar;

(e) recycling said removed α-hydroxysulfonic acid to step (b) as components or in its recombined form; and (f) recycling at least a portion of the bulk liquid stream from (d) to step (b); wherein the bulk liquid stream comprise greater than about 2 wt % of the fermentable sugar based on the bulk liquid stream.

In yet another embodiment, a process comprises further hydrolyzing the wet solids stream.

The features and advantages of the invention will be apparent to those skilled in the art. While numerous changes may be made by those skilled in the art, such changes are within the spirit of the invention.

BRIEF DESCRIPTION OF THE DRAWING

This drawing illustrates certain aspects of some of the embodiments of the invention, and should not be used to limit or define the invention.

DETAILED DESCRIPTION OF THE INVENTION

Figure 1:
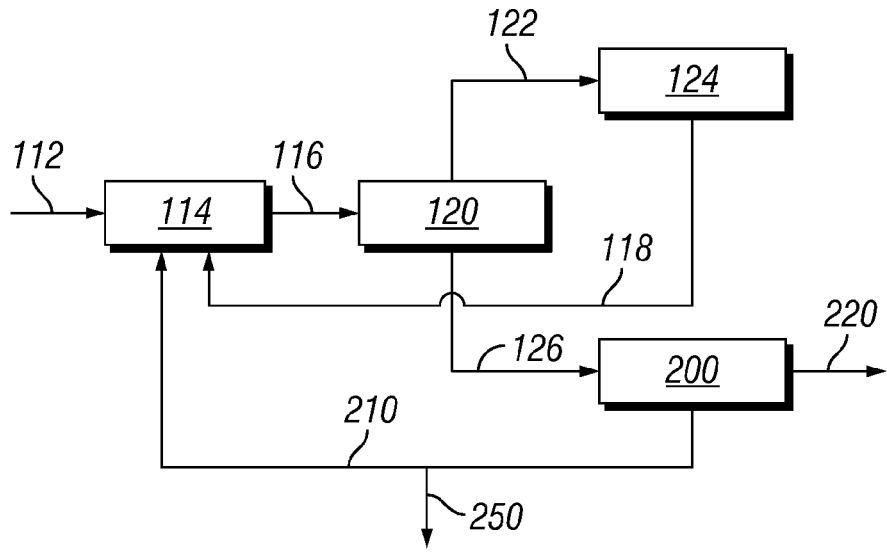
FIG. 1 schematically illustrates a block flow diagram of lignocellulose pretreatments.

As one reduces the amount of water to biomass additional complications ensue. At biomass to water weight ratios, typically known as consistency, over about 12% to 15% the mixture is no longer a pumpable solution, but rather behaves as a wet solid. The equipment required for processing these wet solids or high consistency mixtures (moving, mixing and heat transfer) becomes more expensive, energy inefficient and cumbersome. Knowledge of how to scale up these new, untested pieces of equipment further complicates the development of the new fuel production processes.

It has been found that the present invention provides an improved method for a commercial scale pretreatment of biomass in a process for producing sugars and biofuels. The inventive process incorporates a recyclable recoverable acid in a pumpable pretreatment process that results in a high sugar, high solids biomass, low water pretreated mixture with very little residual acidity (lower salts) and low levels of pretreatment produced toxins (such as furfural).

The low temperature pretreatment process makes a liquid/solid substrate (wet solids stream) that hydrolyzes the same as or better in the presence of the pretreatment liquids than if the pretreated solids are rinsed free of pretreatment liquors in contrast to the process reported in the article by Humbird, D. et al.

The α-hydroxysulfonic acid is effective for treatment of biomass hydrolyzing the biomass to fermentable sugars like pentose such as xylose at lower temperature, (e.g., about 100° C. for α-hydroxymethane sulfonic acid or α-hydroxyethane sulfonic acid) producing little furfural in the process. A portion of the cellulose has also been shown to hydrolyze under these comparatively mild conditions. It has been found that other polysaccharides such as starch are also readily hydrolyzed to component sugars by α-hydroxy sulfonic acids. Further, the α-hydroxysulfonic acid is reversible to readily removable and recyclable materials unlike mineral acids such as sulfuric, phosphoric, or hydrochloric acid. The lower temperatures and pressures employed in the biomass treatment leads to lower equipment cost. The ability to recycle fragile pentose sugars from the end of pretreatment to the inlet of pretreatment, without their subsequent conversion to undesirable materials such as furfural, allows lower consistencies in the pretreatment reaction itself, yet still passing a high consistency solids mixture containing high soluble sugars out of pretreatment. Biomass pretreated in this manner has been shown to be highly susceptible to additional saccharification, especially enzyme mediated saccharification.

Using pretreatment at high temperatures and dilute acid, free xylose is readily dehydrated to form a toxic byproduct, furfural. Thus, in elevated temperature dilute acid processes it is desirable to terminate the pretreatment reaction as soon as the majority of the xylan has been hydrolyzed in order to minimize xylose decomposition. Any free sugars recycled into the front end of an elevated temperature pretreatment process would immediately decompose and result in very high levels of furfurals with no real increase of sugars. This would preclude any attempts at recycling pretreatment liquids to build soluble sugar levels. Thus, in higher temperature, once through pretreatments, the amount of acid solution to "dry weight" biomass introduced in pretreatment determines the ultimate concentration of fermentable sugar obtained. This is balanced by the absorptive nature of biomass with mixing, transport and heat transfer becoming increasingly difficult as the relative amount of biomass solids to liquid is increased. The process of the invention utilizes low severity conditions (e.g. low temperature) that are possible with pretreatment using higher concentrations of α-hydroxysulfonic acids, enabling the recycle and build up of sugars in the pre-treatment reactor stage. The lower temperature process dramatically reduces the rate of C5 and C6 sugar decomposition to other species such as furfural. Thus, free sugars can be introduced (via recycle) into the front end of a low temperature process and they will pass largely unchanged through pretreatment. This allows build up of high concentrations of steady state sugars while handling lower consistency in the pretreatment process. The lower temperature has other advantages as if the temperatures are below the reported lignin melting point, the lignin in the biomass is largely unaltered in texture which results in a non-fouling free flowing pre-treated material. This enables a facile liquid/solid separation at the end of the pretreatment. Using this invention results in a high consistency biomass slurry with high concentrations of soluble sugars and low inhibitors such as furfural. The ultimate undissolved solids concentration passed from pretreatement is thus determined by the ratio of fresh water and biomass put into the front of the process.

The alpha-hydroxysulfonic acids of the general formula

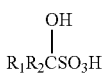

where $R_1$ and $R_2$ are individually hydrogen or hydrocarbyl with up to about 9 carbon atoms that may or may not contain oxygen can be used in the treatment of the instant invention. The alpha-hydroxysulfonic acid can be a mixture of the aforementioned acids. The acid can generally be prepared by reacting at least one carbonyl compound or precursor of carbonyl compound (e.g., trioxane and paraformaldehyde) with sulfur dioxide or precursor of sulfur dioxide (e.g., sulfur and oxidant, or sulfur trioxide and reducing agent) and water according to the following general equation 1.

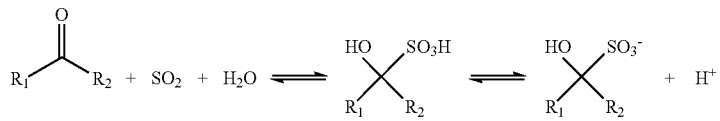

where $R_1$ and $R_2$ are individually hydrogen or hydrocarbyl with up to about 9 carbon atoms or a mixture thereof.

Illustrative examples of carbonyl compounds useful to prepare the alpha-hydroxysulfonic acids used in this invention are found where
$R_1=R_2=H$ (formaldehyde)
$R_1=H$, $R_2=CH_3$ (acetaldehyde)
$R_1=H$, $R_2=CH_2CH_3$ (propionaldehyde)
$R_1=H$, $R_2=CH_2CH_2CH_3$ (n-butyraldehyde) $R_1=H$, $R_2=CH(CH_3)_2$ (i-butyraldehyde)
$R_1=H$, $R_2=CH_2OH$ (glycolaldehyde)
$R_1=H$, $R_2=CHOHCH_2OH$ (glyceraldehdye)
$R_1=H$, $R_2=C(=O)H$ (glyoxal)

$R_1=R_2=CH_3$ (acetone)
$R_1=CH_2OH$, $R_2=CH_3$ (acetol)
$R_1=CH_3$, $R_2=CH_2CH_3$ (methyl ethyl ketone)
$R_1=CH_3$, $R_2=CHC(CH_3)_2$ (mesityl oxide)
$R_1=CH_3$, $R_2=CH_2CH(CH_3)_2$ (methyl i-butyl ketone)
$R_1$, $R_2=(CH_2)_5$ (cyclohexanone) or
$R_1=CH_3$, $R_2=CH_2Cl$ (chloroacetone)

The carbonyl compounds and its precursors can be a mixture of compounds described above. For example, the mixture can be a carbonyl compound or a precursor such as, for example, trioxane which is known to thermally revert to formaldehyde at elevated temperatures, metaldehdye which is known to thermally revert to acetaldehyde at elevated temperatures, or an alcohol that maybe converted to the aldehyde by dehydrogenation of the alcohol to an aldehyde by any known methods. An example of such a conversion to aldehyde from alcohol is described below. An example of a source of carbonyl compounds maybe a mixture of hydroxyacetaldehyde and other aldehydes and ketones produced from fast pyrolysis oil such as described in "Fast Pyrolysis and Bio-oil Upgrading, Biomass-to-Diesel Workshop", Pacific Northwest National Laboratory, Richland, Wash., Sep. 5-6, 2006. The carbonyl compounds and its precursors can also be a mixture of ketones and/or aldehydes with or without alcohols that may be converted to ketones and/or aldehydes, preferably in the range of 1 to 7 carbon atoms.

The preparation of α-hydroxysulfonic acids by the combination of an organic carbonyl compounds, $SO_2$ and water is a general reaction and is illustrated in equation 2 for acetone.

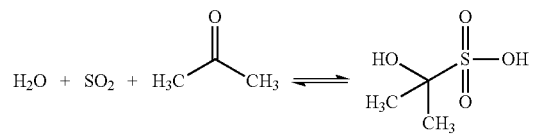

The α-hydroxysulfonic acids appear to be as strong as, if not stronger than, HCl since an aqueous solution of the adduct has been reported to react with NaCl freeing the weaker acid, HCl (see U.S. Pat. No. 3,549,319). The reaction in equation 1 is a true equilibrium, which results in facile reversibility of the acid. That is, when heated, the equilibrium shifts towards the starting carbonyl, sulfur dioxide, and water (component form). If the volatile components (e.g. sulfur dioxide) is allowed to depart the reaction mixture via vaporization or other methods, the acid reaction completely reverses and the solution becomes effectively neutral. Thus, by increasing the temperature and/or lowering the pressure, the sulfur dioxide can be driven off and the reaction completely reverses due to Le Châtelier's principle, the fate of the carbonyl compound is dependant upon the nature of the material employed. If the carbonyl is also volatile (e.g. acetaldehyde), this material is also easily removed in the vapor phase. Carbonyl compounds such as benzaldehyde, which are sparingly soluble in water, can form a second organic phase and be separated by mechanical means. Thus, the carbonyl can be removed by conventional means, e.g., continued application of heat and/or vacuum, steam and nitrogen stripping, solvent washing, centrifugation, etc. Therfore, the formation of these acids is reversible in that as the temperature is raised, the sulfur dioxide and/or aldehyde and/or ketone can be flashed from the mixture and condensed or absorbed elsewhere in order to be recycled. It has been found that these reversible acids, which are approximately as strong as strong mineral acids, are effective in biomass treatment reactions. We have found that these treatment reactions produce very few of the undesired byproducts, furfurals, produced by other conventional mineral acids. Additionally, since the acids are effectively removed from the reaction mixture following treatment, neutralization with base and the formation of salts to complicate downstream processing is substantially avoided. The ability to reverse and recycle these acids also allows the use of higher concentrations than would otherwise be economically or environmentally practical. As a direct result, the temperature employed in biomass treatment can be reduced to diminish the formation of byproducts such as furfural or hydroxymethylfurfural.

It has been found that the position of the equilibrium given in equation 1 at any given temperature and pressure is highly influenced by the nature of the carbonyl compound employed, steric and electronic effects having a strong influence on the thermal stability of the acid. More steric bulk around the carbonyl tending to favor a lower thermal stability of the acid form. Thus, one can tune the strength of the acid and the temperature of facile decomposition by the selection of the appropriate carbonyl compound.

In one embodiment, the acetaldehyde starting material to produce the alpha-hydroxysulfonic acids can be provided by converting ethanol, produced from the fermentation of the treated biomass of the invention process, to acetaldehyde by dehydrogenation or oxidation. Dehydrogenation may be typically carried out in the presence of copper catalysts activated with zinc, cobalt, or chromium. At reaction temperatures of about 260-290° C., the ethanol conversion per pass is 30-50% and the selectivity to acetaldehyde is between 90 and 95 mol %. By-products include crotonaldehyde, ethyl acetate, and higher alcohols. Acetaldehyde and unconverted ethanol are separated from the exhaust hydrogen-rich gas by washing with ethanol and water. Pure acetaldehyde is recovered by distillation, and an additional column is used to separate ethanol for recycle from higher-boiling products. It may not be necessary to supply pure aldehdye to the α-hydroxysulfonic acid process above and the crude stream may suffice. The hydrogen-rich off-gas is suitable for hydrogenation reactions or can be used as fuel to supply some of the endothermic heat of the ethanol dehydrogenation reaction. The copper-based catalyst has a life of several years but requires periodic regeneration. In an oxidation process, ethanol maybe converted to acetaldehyde in the presence of air or oxygen and using a silver catalyst in the form of wire gauze or bulk crystals. Typically, the reaction is carried out at temperatures between 500° and 600° C., depending on the ratio of ethanol to air. Part of the acetaldehyde is also formed by dehydrogenation, with further combustion of the hydrogen to produce water. At a given reaction temperature, the endothermic heat of dehydrogenation partly offsets the exothermic heat of oxidation. Ethanol conversion per pass is typically between 50 and 70%, and the selectivity to acetaldehyde is in the range of 95 to 97 mol %. By-products include acetic acid, CO and $CO_2$. The separation steps are similar to those in the dehydrogenation process, except that steam is generated by heat recovery of the reactor effluent stream. The off-gas steam consists of nitrogen containing some methane, hydrogen, carbon monoxide and carbon dioxide; it can be used as lean fuel with low calorific value. An alternative method to produce acetaldehyde by air oxidation of ethanol in the presence of a Fe—Mo catalyst. The reaction can be carried out at about 180-240° C. and atmospheric pressure using a multitubular reactor. According to patent examples, selectivities to acetaldehyde between 95 and 99 mol % can be obtained with ethanol conversion levels above 80%.

As used herein, the term "biomass" means organic materials produced by plants (e.g., leaves, roots, seeds and stalks). Common sources of biomass include: agricultural wastes (e.g., corn stalks, straw, seed hulls, sugarcane leavings, bagasse, nutshells, and manure from cattle, poultry, and hogs); wood materials (e.g., wood or bark, sawdust, timber slash, and mill scrap); municipal waste (e.g., waste paper and yard clippings); and energy crops (e.g., poplars, willows, switch grass, alfalfa, prairie bluestream, corn, soybean, algae and seaweed). The term "biomass" also refers to the primary building blocks of all the above, including, but not limited to, saccharides, lignins, celluloses, hemicelluloses, and starches. The term "polysaccharides" refers to polymeric carbohydrate structures, of repeating units (either mono- or di-saccharides) joined together by glycosidic bonds. These structures are often linear, but may contain various degrees of branching. Examples include storage polysaccharides such as starch and glycogen, and structural polysaccharides such as cellulose and chitin. The biomass is typically preprocessed to suitable particles size that may include grinding. Not intending to restrict the scope of the invention, it is typically found that it is easier to process smaller particles of biomass. Biomass that is size reduced to facilitate handling (e.g. less than 1.3 cm) are particularly susceptible materials.

Various factors affect the conversion of the biomass feedstock in the hydrolysis reaction. The carbonyl compound or incipient carbonyl compound (such as trioxane) with sulfur dioxide and water should be added to in an amount and under conditions effective to form alpha-hydroxysulfonic acids. The temperature and pressure of the hydrolysis reaction should be in the range to form alpha-hydroxysulfonic acids and to hydrolyze biomass into fermentable sugars. The amount of carbonyl compound or its precursor and sulfur dioxide should be to produce alpha-hydroxysulfonic acids in the range from about 1 wt %, preferably from about 5 wt %, to about 55 wt %, preferably to about 40 wt %, more preferably to about 20 wt %, based on the total solution. For the reaction, excess sulfur dioxide is not necessary, but any excess sulfur dioxide may be used to drive the equilibrium in eq. 1 to favor the acid form at elevated temperatures. The contacting conditions of the hydrolysis reaction may be conducted at temperatures preferably at least from about 50° C. depending on the alpha-hydroxysulfonic acid used, although such temperature may be as low as room temperature depending on the acid and the pressure used. The contacting condition of the hydrolysis reaction may range preferably up to and including about 150° C. depending on the alpha-hydroxysulfonic acid used. In a more preferred condition the temperature is at least from about 80° C., most preferably at least about 100° C. In a more preferred condition the temperature range up to and including about 90° C. to about 120° C. The reaction is preferably conducted at as low a pressure as possible, given the requirement of containing the excess sulfur dioxide. The reaction may also be conducted at a pressure as low as about 1 barg, preferably about 4 barg, to about pressure of as high as up to 10 barg. The temperature and pressure to be optimally utilized will depend on the particular alpha-hydroxysulfonic acid chosen and optimized based on economic considerations of metallurgy and containment vessels as practiced by those skilled in the art.

Numerous methods have been utilized by those skilled in the art to circumvent these obstacles to mixing, transport and heat transfer. Thus weight percentage of biomass solids to total liquids (consistency) may be as low as 1% or higher depending on the apparatus chosen and the nature of the biomass (even as high as 33% if specialized equipment is developed or used). The solids percent is weight percent of dry solids basis and the wt % liquids contains the water in the biomass. In the preferred emobidment, where a more conventional equipment is desired, then the consistency is from at least 1 wt %, preferably at least about 2 wt %, more preferably at least about 8 wt %, up to about 25 wt %, preferably to about 20 wt %, more prefearably to about 15 wt %.

The temperature of the hydrolysis reaction can be chosen so that the maximum amount of extractable carbohydrates are hydrolyzed and extracted as fermentable sugar (more preferably pentose and/or hexose) from the biomass feedstock while limiting the formation of degradation products. The temperatures required for successful pretreatment are controlled by the reaction time, the pH of the solution (acid concentration), and the reaction temperature. Thus as the acid concentration is raised, the temperature may be reduced and/or the reaction time extended to accomplish the same objective. The advantages of lowering the reaction temperature are that the fragile monomeric sugars are protected from degradation to dehydrated species such as furfurals and that the lignin sheath is not dissolved or melted and re-deposited upon the biomass. If high enough levels of acid are employed, temperatures can be reduced below the point at which sugar degredation or lignin deposition are problematic; this in turn is made possible through the use of reversible α-hydroxysulfonic acids. In such a low temperature process it becomes possible to recycle a sugars mixture from the back of a pretreatment process to the front of a pretreatment process. This allows the sugars to build to a high steady state value while still handling a pumpable slurry through the pretreatment process. Such a process is outlined in the scheme below. In this process biomass, water, and α-hydroxysulfonic acid are combined in an acid hydrolysis step and reacted to effect biomass pretreatment. The acids are separated from the reaction mixture as described above and recycled to the pretreatment reactor. Then a concentrated high solids/liquid mixture (wet solid stream) is separated from the bulk liquid, which is recycled to the reactor as well. In this manner the biomass to liquids ratio is set by the feed ratio of these components and the optimized target of wet biomass to move into enzymatic hydrolysis.

In some embodiments, a plurality of reactor vessels may be used to carry out the hydrolysis reaction. These vessels may have any design capable of carrying out a hydrolysis reaction. Suitable reactor vessel designs can include, but are not limited to, batch, trickle bed, co-current, counter-current, stirred tank, down flow, or fluidized bed reactors. Staging of reactors can be employed to arrive the most economical solution. The remaining biomass feedstock solids may then be optionally separated from the liquid stream to allow more severe processing of the recalcitrant solids or pass directly within the liquid stream to further processing that may include enzymatic hydrolysis, fermentation, extraction, distillation and/or hydrogenation. In another embodiment, a series of reactor vessels may be used with an increasing temperature profile so that a desired sugar fraction is extracted in each vessel. The outlet of each vessel can then be cooled prior to combining the streams, or the streams can be individually fed to the next reactor for conversion.

Suitable reactor designs can include, but are not limited to, a backmixed reactor (e.g., a stirred tank, a bubble column, and/or a jet mixed reactor) may be employed if the viscosity and characteristics of the partially digested bio-based feedstock and liquid reaction media is sufficient to operate in a regime where bio-based feedstock solids are suspended in an excess liquid phase (as opposed to a stacked pile digester). It is also conceivable that a trickle bed reactor could be employed with the biomass present as the stationary phase and a solution of α-hydroxysulfonic acid passing over the material.

In some embodiments, the reactions described below are carried out in any system of suitable design, including systems comprising continuous-flow (such as CSTR and plug flow reactors), batch, semi-batch or multi-system vessels and reactors and packed-bed flow-through reactors. For reasons strictly of economic viability, it is prefferable that the invention is practiced using a continuous-flow system at steady-state equilibrium. In one advantage of the process in contrast with the dilute acids pretreatment reactions where residual acid is left in the reaction mixture (<1% wt. sulfuric acid), the lower temperatures employed using these acids (5 to 20% wt.) results in substantially lower pressures in the reactor resulting in potentially less expensive processing systems such as plastic lined reactors, duplex stainless reactors, for example, such as 2205 type reactors.

FIG. 1 shows an embodiment of the present invention for converting biomass into sugars. In this embodiment, a biomass feedstock 112 is introduced to a hydrolysis reaction system 114 along with a recycle stream 118. The hydrolysis reaction system114 can comprise a number of components including in situ generated α-hydroxysulfonic acid. The term "in situ" as used herein refers to a component that is produced within the overall process; it is not limited to a particular reactor for production or use and is therefore synonymous with an in process generated component. The hydrolysis reaction system 114 can contain one or more reactors and optionally solids or slurry extractors. The reacted product stream 116 from 114 is introduced to acid removal system 120 where the acid is removed in its component form then is recovered 122 (and optionally scrubbed 124) and recycled via recycle stream 118 to 114 and product stream 126 containing at least one fermentable sugar (e.g., pentose and optionally hexose) substantially without the alpha-hydroxysulfonic acids is produced. Optionally, at least a portion of the liquid on product stream 116 containing α-hydroxysulfonic acid can be recycled to the hydrolysis reaction system 114. The product stream 126 is provided to a separation system 200 where a high solids/liquid mixture is separated from the acid-removed product stream to form a wet solids stream 220 containing at least 12 wt % undissolved solids containing cellulose, preferably in the range of 15 wt % to 35% wt undissolved solids, and more preferably in the range of 20 to 25 wt % undissolved solids, based on the wet solds stream, and a bulk liquid stream 210 that may constitute up to 20 to 80 wt % of the liquid from the acid-removed product stream that contains fermentable sugar (e.g., pentose and optionally hexose). At least a portion of the bulk liquid stream 210 is recycled to the hydrolysis reaction system where the bulk liquid stream comprise greater than about 2 wt %, preferably 5 wt % or greater, more preferably about 8 wt % or greater, of fermentable sugar based on the bulk liquid stream. The bulk liquid stream is recycled in such a manner as to keep the hydrolysis reaction pumpable, preferably about 15 wt % or less of solids content in the hydrolysis reactor. As one embodiment, a portion of the bulk liquid recycle stream 210 can be used to dilute the hydrolysis reaction system 114 towards the inlet of the biomass in the hydrolysis reactor in the system, and/or for ease of solids extraction at the reactor bottoms (or reactor system exit) or can be added to a extractor or towards the reactor product stream 116 for dilution. A portion of the bulk liquid stream 210 that contains fermentable sugar can optionally be removed, 250, and further processed to produce biofuel components or other chemicals. Required make up water can be introduced to the primary pretreatment system 114 or in numerous other locations to achieve desired results. For instance required make up water could be introduced into the solids/liquid separation step 200 in a manner to produce a rinsed biomass, allowing the predominental pentose stream to be processed as a separate stream, 250.

Figure 2:
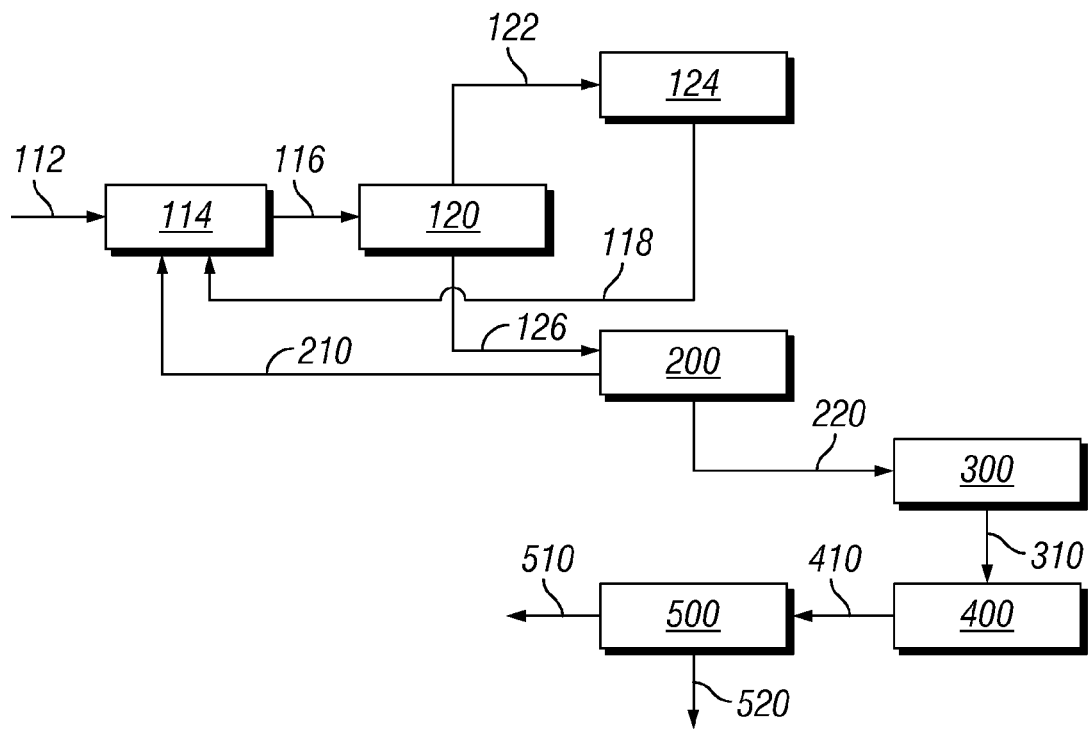
FIG. 2 schematically illustrates a block flow diagram of an embodiment of biomass treatment process of the invention.

FIG. 2 shows an embodiment of the present invention for converting biomass into alcohols. In this embodiment, a biomass feedstock 112 is introduced to a hydrolysis reaction system 114 along with a recycle stream 118. The hydrolysis reaction system 114 can comprise a number of components including in situ generated α-hydroxysulfonic acid. The term "in situ" as used herein refers to a component that is produced within the overall process; it is not limited to a particular reactor for production or use and is therefore synonymous with an in process generated component. The hydrolysis reaction system 114 can contain one or more reactors and optionally solids or slurry extractors. The reacted product stream 116 from 114 is introduced to acid removal system 120 where the acid is removed in its component form then is recovered 122 (and optionally scrubbed 124) and recycled via recycle stream 118 to 114 and product stream 126 containing at least one fermentable sugar (e.g., pentose and optionally hexose) substantially without the alpha-hydroxysulfonic acids is produced. The removed acid as components is recycled to 114 as components and/or in its recombined form. Optionally, at least a portion of the liquid on product stream 116 containing α-hydroxysulfonic acid can be recycled to the hydrolysis reaction system 114. The product stream 126 is provided to a separation system 200 where a high solids/liquid mixture is separated from the acid-removed product stream to form a wet solids stream 220 containing at least 12 wt % undissolved solids containing cellulose, preferably in the range of 15 wt % to 35 wt % undissolved solids, more preferably in the range of 20 wt % to 25 wt % undissolved solids, based on the wet solids stream, and a bulk liquid stream 210 that may constitute up to 20 to 80 wt % of the liquid from the acid-removed product stream that contains fermentable sugar (e.g., pentose and optionally hexose). At least a portion of the bulk liquid stream 210 is recycled to the hydrolysis reaction where the bulk liquid stream comprise greater than about 2 wt %. preferably about 5 wt % or greater, more preferably about 8 wt % or greater, of fermentable sugar based on the bulk liquid stream. The bulk liquid stream is recycled in such a manner as to keep the hydrolysis reaction pumpable, preferably about 15 wt % or less of solids content in the hydrolysis reactor. As one embodiment, a portion of the bulk liquid recycle stream 210 can be used to dilute the hydrolysis reaction system 114 towards the inlet of the biomass in the hydrolysis reactor in the system, and/or for ease of solids extraction at the reactor bottoms (or reactor system exit) or can be added to a extractor or towards the reactor product stream 116 for dilution. At least a portion of the wet solids stream 220 can optionally be provided to a wash system that may have one or more washing steps with water. It is one of the features of the invention that the wash step may not be necessary due to the composition of product stream and the wet solids stream produced by the continuous or semi-continuous process of the invention. If wash step is employed, a liquid wash stream (not shown in the figure) can be pass back to the pretreatment reactor 114 as a portion of the water inlet stream, and/or be provided to the separation system 200. At least a portion of the bulk liquid stream 210 can optionally be processed to remove and recover any acetic acid present. At least a portion of the bulk liquid stream 210, comprised primarily of pentose sugars in water can be process independently to products or recombined with the hydrolyzate 310 as a feed to the fermentation system 400. The (optionally washed) wet solids stream 220 is provided to the enzymatic hydrolysis system 300 as as high solids feedstock to the enzymatic hydrolysis system. In the enzymatic hydrolysis system 300, pretreated biomass, and optionally hemicelluloses from a potion of the bulk solution stream, is hydrolyzed with an enzyme solution, whereby hydrolyzate (aqueous sugar stream) 310 is produced and fermented in the fermentation system 400 in the presence of a microorganism(s) to produce a fermented product stream containing at least one alcohol (alcohol stream 410). The alcohol 510 can then be recovered in a recovery system 500 from the alcohol stream 410 also producing aqueous effluent stream 520. Lignin can be optionally removed (not shown) after the enzyme hydrolysis system, after the fermentation system or after the recovery system by lignin separation system. The aqueous effluent stream after the removal of lignin can be optionally recycled as aqueous effluent recycle stream to the hydrolysis reaction thereby reducing fresh water intake in the overall process.

The treatment reaction product contains fermentable sugar or monosaccharides, such as pentose and/or hexose that is suitable for further processing. Optionally, at least a portion of the liquid stream containing the residual alpha-hydroxysulfonic acid from the fermentable sugar containing product stream may be recycled to the treatment reaction. The residual alpha-hydroxysulfonic acid can be removed by application of heat and/or vacuum from the fermentable sugar containing product stream to reverse the formation of alpha-hydroxysulfonic acid to its starting material to produce a stream containing fermentable sugar substaintially free of the α-hydroxysulfonic acid. In particular, the product stream is substantially free of alpha-hydroxysulfonic acid, meaning no more than about 2 wt % is present in the product stream, preferably no more than about 1 wt %, more preferably no more than about 0.2 wt %, most preferably no more than about 0.1 wt % present in the product stream. The temperature and pressure will depend on the particular alpha-hydroxysulfonic acid used and minimization of temperatures employed are desirable to preserve the sugars obtain in treatment reactions. Typically the removal may be conducted at temperatures in the range from about 50° C., preferably from about 80° C., more preferably from 90° C., to about 110° C., up to about 150° C. The pressure may be in the range of from about 0.5 bara, to about 2 barg, more preferably from 0.1 barg to about 1 barg. It can be appreciated by a person skill in the art that the treatment reaction 114 and the removal of the acid 120 can occurred in the same vessel or a different vessel or in a number of different types of vessels depending on the reactor configuration and staging as long as the system is designed so that the reaction is conducted under condition favorable for the formation and maintainence of the alpha-hydroxysulfonic acid and removal favorable for the reverse reaction (as components). As an example, the reaction in the reactor vessel 114 can be operated at approximately 100° C. and a pressure of 4 barg in the presence of alpha-hydroxyethanesulfonic acid and the removal vessel 120 can be operated at approximately 110° C. and a pressure of 0.5 barg. It is further contemplated that the reversion can be favored by the reactive distillation of the formed alpha-hydroxysulfonic acid. In the recycling of the removed acid, optionally additional carbonyl compounds, $SO_2$, and water may be added as necessary. The removed starting material and/or alpha-hydroxysulfonic acid may be condensed and/or scrubbed by contact with water and recycled to the reaction system 114 as components or in its recombined form.

The preferable residence time of the biomass to contact with the α-hydroxysulfonic acid in the hydrolysis reaction system may be in the range of about 5 minutes to about 4 hours, most preferably about 15 minutes to about 1 hour.

Thus, a typical hydrolysis reaction mixture contains (a) biomass containing polysaccharides, (b) at least one α-hydroxysulfonic acid, (c) water, and (d) at least one fermentable sugar. It has been found that a beta-sulfo aldehyde or ketone compound forms in the reaction mixture with time and acid concentration. It will build to steady state with liquid recycle in the continuous or semi-continuous process of the invention. After the α-hydroxysulfonic acid is removed, the bulk liquid streamed is removed, the wet solids stream may contain (a) biomass containing polysaccharides (undissolved solids), (b) water, and (c) at least one beta-sulfo aldehyde or ketone compound. Without intent to be bound by the theory, it is thought that the very little acidity (lower salts) and low levels of pretreatment produced toxins (such as furfural)

allows the wet solids to be further enzyme hydrolyzed without prior wash steps as required for conventional biomass pretreatment processes. Further, without intent to be bound by the theory, it is thought that the presence of a beta-sulfo aldehyde or ketone compound that is present in a concentration of at least 0.01 wt %, preferably at least 0.03 wt %, more preferably at least about 0.5 wt %, up to 5 wt %, more preferably upto about 2 wt %, based on wet solids stream, may help facilitate the enzyme hydrolysis.

It is thought that the beta-sulfo aldehyde or ketone compound has the following general formula:

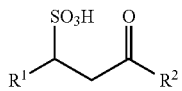

wherein $R^1$ and $R^2$ are individually hydrogen or hydrocarbyl with up to about 9 carbon atoms. Sulfonated crotonalde where $R^1$ is a methyl group and $R^2$ is hydrogen is preferred.

The separation system can be carried out by any separation method to separate wet solids and liquids. Exmples of suitable separation method, for example, may include centrifugal force, filtration, decantation, and other like methods.

In one embodiment, the cellulose containing product stream can further be hydrolyzed by other methods, for example by enzymes to further hydrolyze the biomass to sugar products containing pentose and hexose (e.g., glucose) and fermented to produce alcohols such as disclosed in US Publication No. 2009/0061490 and U.S. Pat. No. 7,781,191 which disclosures are hereby incorporated by reference.

In yet another embodiment, the fermentable sugar can be converted to furfural or hydroxymethylfurfural (HMF) or further fermented to alcohols. Although in some embodiments it may be desirable to minimize the formation of furfurals, if formation of furfurals is desired, the acid containing solution of step (b) may be further heated to a temperature in the range of from 110 to 160° C., more preferably in the range of from 120 to 150° C. to form at least one furfural containing product stream. In one embodiment, the temperature of step (b) is maintained to a temperature of 100° C. or less if it is desirable to obtain minimal furfural in the product stream.

In yet another embodiment, the fermentable sugars can be converted to higher hydrocarbons as a biofuel component using catalytic hydrogenation and condensation techniques rather than further hydrolysis by enzyme and fermentation. Typically the fermentable sugar containing product is contacted with hydrogen in the presence of a hydrogenolysis catalyst to form a plurality of oxygenated intermediates, and then further processing the oxygenated intermediates to produce a fuel blend in one or more processing reactions. In an embodiment, a condensation reaction can be used along with other reactions to generate a fuel blend and may be catalyzed by a catalyst comprising acid or basic functional sites, or both to product a liquid fuel. As used herein, the term "higher hydrocarbons" refers to hydrocarbons having an oxygen to carbon ratio less than at least one component of the biomass feedstock. As used herein the term "hydrocarbon" refers to an organic compound comprising primarily hydrogen and carbon atoms, which is also an unsubstituted hydrocarbon. In certain embodiments, the hydrocarbons of the invention also comprise heteroatoms (e.g., oxygen or sulfur) and thus the term "hydrocarbon" may also include substituted hydrocarbons.

In one such example, the fermentable sugar containing product stream may be further processed to produce mixtures of C4+ compounds useful for biofuels such as described in U.S. Publication Nos. US2011/0154721 and US2011/0282115 which disclosures are hereby incorporated by reference. As another such example, the fermentable sugar containing product stream may be further processed to produce mixtures of C4+ compounds useful for biofuels such as described in U.S. Publication No. 20080216391 which disclosure is hereby incorporated by reference. The solid feed may also be suitable for use in fast pyrrolysis reactions leading to fuels and chemicals.

The term "fermentable sugar" refers to oligosaccharides and monosaccharides that can be used as a carbon source (e.g., pentoses and hexoses) by a microorganism in a fermentation process. It is contemplated that fermentable sugar may be fermented as described above, but may also be processed by other methods without fermentation to produce fuels as described above. The term "pentose" refers to monosaccharides with five carbon atoms. The term "hexose" refers to monosaccharides with six carbon atoms.

In an enzymatic hydrolysis-fermentation processes the pH of the pretreated feedstock to the enzymatic hydrolysis is typically adjusted so that it is within a range which is optimal for the cellulase enzymes used. Generally, the pH of the pretreated feedstock is adjusted to within a range of about 3.0 to about 7.0, or any pH there between.

The temperature of the treated feedstock is adjusted so that it is within the optimum range for the activity of the cellulase enzymes. Generally, a temperature of about 15° C. to about 100° C., about 20° C. to about 85° C., about 30° C. to about 70° C. preferably or any temperature there between, is suitable for most cellulase enzymes. The cellulases, β-glucosidase and other accessory enzymes required for cellulose hydrolysis are added to the pretreated feedstock, prior to, during, or after the adjustment of the temperature and pH of the aqueous slurry after pretreatment. Preferably the enzymes are added to the pretreated lignocellulosic feedstock after the adjustment of the temperature and pH of the slurry.

By the term "cellulase enzymes" or "cellulases," it is meant a mixture of enzymes that hydrolyze cellulose. The mixture may include cellobiohydrolases (CBH), glucobiohydrolases (GBH), endoglucanases (EG), glycosyl hydrolyase family 61 proteins (GH61) and β-glucosidase. By the term "β-glucosidase", it is meant any enzyme that hydrolyzes the glucose dimer, cellobiose, to glucose. In a non-limiting example, a cellulase mixture may include EG, CBH, GH61 and β-glucosidase enzymes.

The enzymatic hydrolysis may also be carried out in the presence of one or more xylanase enzymes. Examples of xylanase enzymes that may also be used for this purpose and include, for examples, xylanase 1, 2 (Xyn1 and Xyn2) and β-xylosidase, which are typically present in cellulase mixtures.

The process can be carried out with any type of cellulase enzymes, regardless of their source. Non-limiting examples of cellulases which may be used include those obtained from fungi of the genera *Aspergillus, Humicola,* and *Trichoderma, Myceliophthora, Chrysosporium* and from bacteria of the genera *Bacillus, Thermobifida* and *Thermotoga*. In some embodiments, the filamentous fungal host cell is an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

The cellulase enzyme dosage is chosen to convert the cellulose of the pretreated feedstock to glucose. For example, an appropriate cellulase dosage can be about 1 to about 100 mg enzyme (dry weight) per gram of cellulose.

In practice, the hydrolysis may carried out in a hydrolysis system, which may include a series of hydrolysis reactors. The number of hydrolysis reactors in the system depends on the cost of the reactors, the volume of the aqueous slurry, and other factors. The enzymatic hydrolysis with cellulase enzymes produces an aqueous sugar stream (hydrolyzate) comprising glucose, unconverted cellulose, lignin and other sugar components. The hydrolysis may be carried out in two stages (see U.S. Pat. No. 5,536,325, which is incorporated herein by reference), or may be performed in a single stage.

In the fermentation system, the aqueous sugar stream is then fermented by one or more than one fermentation microorganism to produce a fermentation broth comprising the alcohol fermentation product useful as biofuels. In the fermentation system, any one of a number of known microorganisms (for example, yeasts or bacteria) may be used to convert sugar to ethanol or other alcohol fermentation products. The microorganisms convert sugars, including, but not limited to glucose, mannose and galactose present in the clarified sugar solution to a fermentation product.

Many known microorganisms can be used in the present process to produce the desired alcohol for use in biofuels. Clostridia, Escherichia coli (E. coli) and recombinant strains of E.coli, genetically modified strain of Zymomonas mobilis such as described in US2003/0162271, U.S. Pat. Nos. 7,741,119 and 7,741,084 (which disclosures are herein incorporated by reference) are some examples of such bacteria. The microorganisms may further be a yeast or a filamentous fungus of a genus Saccharomyces, Kluyveromyces, Candida, Pichia, Schizosaccharomyces, Hansenula, Kloeckera, Schwanniomyces, Yarrowia, Aspergillus, Trichoderma, Humicola, Acremonium, Fusarium, and Penicillium. The fermentation may also be performed with recombinant yeast engineered to ferment both hexose and pentose sugars to ethanol. Recombinant yeasts that can ferment one or both of the pentose sugars xylose and arabinose to ethanol are described in U.S. Pat. Nos. 5,789,210, and 6,475,768, European Patent EP 1,727,890, European Patent EPI 863,901 and WO 2006/096130 which disclosures are herein incorporated by reference. Xylose utilization can be mediated by the xylose reductase/xylitol dehydrogenase pathway (for example, WO9742307 A1 19971113 and WO9513362 A1 19950518) or the xylose isomerase pathway (for example, WO2007028811 or WO2009109631). It is also contemplated that the fermentation organism may also produce fatty alcohols, for example, as described in WO 2008/119082 and PCT/US07/011923 which disclosure is herein incorporated by reference. In another embodiment, the fermentation may be performed by yeast capable of fermenting predominantly C6 sugars for example by using commercially available strains such as Thermosacc and Superstart.

Preferably, the fermentation is performed at or near the temperature and pH optima of the fermentation microorganism. For example, the temperature may be from about 25° to about 55° C., or any amount there between. The dose of the fermentation microorganism will depend on other factors, such as the activity of the fermentation microorganism, the desired fermentation time, the volume of the reactor and other parameters. It will be appreciated that these parameters may be adjusted as desired by one of skill in the art to achieve optimal fermentation conditions.

The fermentation may be conducted in batch, continuous or fed-batch modes, with or without agitation. The fermentation system may employ a series of fermentation reactors.

In some embodiment, the hydrolysis system and fermentation system may be conducted in the same vessel. In one embodiment, the hydrolysis can be partially completed and the partially hydrolyzed stream may be fermented. In one embodiment, a simultaneous saccharification and fermentation (SSF) process where hydrolysis system may be run until the final percent solids target is met and then the hydrolyzed biomass may be transferred to a fermentation system.

The fermentation system produces an alcohol stream preferably containing at least one alcohol having 2 to 18 carbon atoms. In the recovery system, when the product to be recovered in the alcohol stream is a distillable alcohol, such as ethanol, the alcohol can be recovered by distillation in a manner known to separate such alcohol from an aqueous stream. If the product to be recovered in the alcohol stream is not a distillable alcohol, such as fatty alcohols, the alcohol can be recovered by removal of alcohols as solids or as oils from the fermentation vessel, thus separating from the aqueous effluent stream.

While the invention is susceptible to various modifications and alternative forms, specific embodiments thereof are shown by way of examples herein described in detail. It should be understood, that the detailed description thereto are not intended to limit the invention to the particular form disclosed, but on the contrary, the intention is to cover all modifications, equivalents and alternatives falling within the spirit and scope of the present invention as defined by the appended claims. The present invention will be illustrated by the following illustrative embodiment, which is provided for illustration only and is not to be construed as limiting the claimed invention in any way.

ILLUSTRATIVE EMBODIMENTS

General Methods and Materials

In the examples, the aldehyde or aldehyde precursors were obtained from Sigma-Aldrich Co.

Whole wheat straw having the following components analyzed using standard TAPPI methods (T-249, T-222, T-211) and had the following average composition on a dry basis:

| | |
|---|---|
| Glucan | 38.8 wt. % |
| Xylan | 23 wt. % |
| Lignin | 22 wt. % |
| Ash | 5.9 wt. % |
| Other | 10.3 wt % |

Analytical Methods

Determination of Oxygenated Components in Aqueous Layer.

A sample or standard is analyzed by injection into a stream of a mobile phase that flows though a Bio-rad column (Aminex HPX-87H, 300 mm×7.8 mm). The reverse phase HPLC system (Shimadzu) equipped with both RI and UV detectors and the signals are recorded as peaks on a data acquisition and data processing system. The components are quantified using external calibration via a calibration curves based on injection of know concentrations of the target components. Some of the components were calculated by using single point of standard. The reference samples contained 0.5 wt % Glucose, Xylose and Sorbitol in Water HPLC Instrument Conditions:
   Column: Bio-Rad Aminex HPX-87H (300 mm×7.8 mm)
   Flow Rate: 0.6 ml/minute
   Column Oven: 30° C.
   Injection Volumn: 10 μl
   UV Detector: @320 NM
   RI Detector: mode—A; range—100
   Run Time: 70 minute
   Mobile Phase: 5 mM Sulfuric Acid in water
   Sample is either injected directly or diluted with water first, but makes sure there is no particulars. Pass through the 0.2 μm syringe filter, if there is precipitation in the sample or diluted sample. Samples were analyzed for Glucose, Xylose, Formic Acid, Acetic Acid, Arabinose, hydroxymethyl furfural, and Furfural content.

EXAMPLES

General Procedure for the Formation of α-hydroxysulfonic Acids.

Aldehydes and ketones will readily react with sulfur dioxide in water to form α-hydroxy sulfonic acids according to the equation 1 above. These reactions are generally rapid and somewhat exothermic. The order of addition ($SO_2$ to carbonyl or carbonyl to $SO_2$) did not seem to affect the outcome of the reaction. If the carbonyl is capable of aldol reactions, preparation of concentrated mixtures (>30% wt.) are best conducted at temperatures below ambient to minimize side reactions. We have found it beneficial to track the course of the reaction using in situ Infrared Spectroscopy (ISIR) employing probes capable of being inserted into pressure reaction vessels or systems. There are numerous manufacturers of such systems such as Mettler Toledo Autochem's Sentinal probe. In addition to being able to see the starting materials: water (1640 $cm^{-1}$), carbonyl (from approx. 1750 $cm^{-1}$ to 1650 $cm^{-1}$ depending on the organic carbonyl structure) and $SO_2$ (1331 $cm^{-1}$), the formation of the α-hydroxysulfonic acid is accompanied by the formation of characteristic bands of the $SO_3^-$ group (broad band around 1200 $cm^{-1}$) and the stretches of the α-hydroxy group (single to mutiple bands around 1125 $cm^{-1}$). In addition to monitoring the formation of the α-hydroxy sulfonic acid, the relative position of the equilibrium at any temperature and pressure can be readily assessed by the relative peak heights of the starting components and the acid complex. The definitive presence of the α-hydroxy sulfonic acid under biomass hydrolysis conditions can also be confirmed with the ISIR and it is possible to monitor the growth of sugars in the reaction mixture by monitoring the appropriate IR bands.

Example 1

Formation of 40% wt. α-hydroxyethanesulfonic Acid from Metaldehyde.

Into a sealed 2 L Parr autoclave equipped with a DiComp IR probe was charged 999.98 grams of nitrogen sparged deionized water and 212.02 grams of metaldehyde. Two Hoke vessels containing 171.19 and 167 grams, 338.19 grams total, of sulfur dioxide are attached to the reactor as a "blowcase injector". The reactor is closed and pressure tested with nitrogen gas. The stirrer is started at 1000 rpm and IR acquisition initiated. The sulfur dioxide is injected to the reactor through a ball valve and its accumulation in the reaction mixture noted in the IR spectrum with a strong absorption at 1331 $cm^{-1}$. Due to the sparse water solubility of metaldehdye, no absorption bands due to this material are noted. The formation of the α-hydroxysulfonic acid was monitored by in situ IR. After the addition of sulfur dioxide the reactor was heated slowly and at approximately 50° C. the formation of a-hydroxyethane sulfonic acid ensues with bands for this species, a broad band centered about 1175 $cm^{-1}$ and two sharp bands at 1038 $cm^{-1}$ and 1015 $cm^{-1}$, increasing while the bands for sulfur dioxide fall and the temperature rises to a maximum of 68° C. due to exothermic reaction. The reaction was stirred for one hour after completion with no further change in the IR spectrum. The reaction mixture was cooled to room temperature and the residual pressure vented through a caustic scrubber, purging the gas cap several times with nitrogen to eliminate any free sulfur dioxide. The clear light yellow acid solution was transferred to a tared bottle, recovering 1468.74 g of α-hydroxyethane sulfonic acid solution. Proton NMR analysis revealed this to be 36.7% wt. α-hydroxyethane sulfonic acid.

Example 2

Formation of 40% wt. α-hydroxyethanesulfonic Acid from Acetaldehdye

Approximately 245 grams of ice cold acetaldehyde is transferred into 1107 grams of nitrogen degassed cold (<5° C.) water in a 2 liter erlynmeyer flask. The flask was gently agitated to dissolve the acetaldehyde into the water. The solution was warmed to room temperature and 1340.68 grams of aqueous solution containing 242.77 grams of acetaldehyde was transferred into a 2000 ml Parr autoclave fitted with IR optics. The reactor and contents is then cooled so that the liquid temperature is below 5° C. Two single ended Hoke vessels containing a total of 361.07 grams of sulfur dioxide are connected to the inlet of the reaction vessel as blowcase injectors. The mixture was stirred at 1000 rpm and acquisition of IR data is initiated. The sulfur dioxide is injected into the acetaldehyde/water solution and a rapid exothermic reaction ensues, the temperature of the reaction mixture rising to 39° C. The IR bands of sulfur dioxide and acetaldehyde fall and those for α-hydroxyethane sulfonic acid rise rapidly, indicating the conversion of reactants to product acid. The reaction mixture is allowed to cool to room temperature, vented through a caustic scrubber and the gas cap purged with nitrogen for a few minutes to remove any residual $SO_2$ or acetaldehyde. The reactor contents are transferred into a tared glass bottle. A total of 1691.41 grams is recovered. Proton NMR analysis shows this to be 40.01% wt. α-hydroxyethane sulfonic acid in water with no discernable byproducts Examples 3-7

Pretreatment Reaction with Recycle; 120° C., 15 Minutes, 1500 rpm Strirring

Into a 2 liter C276 Parr reactor fitted with in situ IR optics was added approximately 120 grams of compositionally characterized wheat straw [dry basis: xylan 23 wt %; glucan 38.8 wt %] chopped to nominal 0.5 cm particles. The exact dry weight of biomass is given in column b. To this was added approximately 1000 grams of 5 wt % α-hydroxyethane sulfonic acid (HESA) prepared by the dilution of a 40 wt % stock solution of the acid or acid recycled from vaporization of components at the end of a reaction cycle with de-ionized water. Target concentration of acid was confirmed by proton NMR of the starting mixture integrating over the peaks for water and the acid. The reactor top with a 4 blade down pitch impeller was placed on top of the reaction vessel and the reactor sealed. The pressure integrity of the reactor system and air atmosphere replacement was accomplished by pressurization with nitrogen to 100 psig where the sealed reactor was held for 15 minutes without loss of pressure followed by venting to atmospheric pressure. IR acquisition was initiated and the reaction mixture stirred at 1500 rpm. The reactor was then heated to 120° C. and held at target temperature for 15 minutes. During this period of time the in situ IR reveals the presence of HESA, SO₂, and acetaldehyde in an equilibrium mixture. An increase in sugars is evident in the IR spectra, with an increase in the band height typical of xylose and glucose being apparent. At the end of the reaction period the acid reversal was accomplished via opening the gas cap of the reactor to an overhead condensation system for recovery of the acid and simultaneously adjusting the reactor temperature set point to 100° C. Vaporization from the reactor quickly cools the reactor contents to the 100° C. set point. The overhead condensation system was comprised of a 1 liter jacketed flask fitted with a fiber optic based in situ IR probe, a dry ice acetone condenser on the outlet and the gas inlet arriving through an 18" long steel condenser made from a core of ¼" diameter C-276 tubing fitted inside of ½" stainless steel tubing with appropriate connections to achieve a shell-in-tube condenser draining downward into the recovery flask. The recovery flask was charged with approximately 400 grams of DI water and the condenser and jacketed flask cooled with a circulating fluid held at 1° C. The progress of the acid reversion was monitored via the use of in situ IR in both the Parr reactor and the overhead condensation flask. During the reversal the first component to leave the Parr reactor was $SO_2$ followed quickly by a decrease in the bands for HESA. Correspondingly the bands for $SO_2$ rise in the recovery flask and then quickly fall as HESA was formed from the combination of vaporized acetaldehyde with this component. The reversal was continued until the in situ IR of the Parr reactor showed no remaining traces of the α-hydroxyethane sulfonic acid. The IR of the overheads revealed that the concentration of the HESA at this point had reached a maximum and then started to decrease due to dilution with condensed water, free of α-hydroxyethane sulfonic acid components, building in the recovery flask. The total mass of material condensed overhead is given in column c. The condensate is analyzed via proton NMR to determine the recovery of the α-hydroxyethane sulfonic acid employed, this value is given in column d. The reaction mixture was then cooled to room temperature, opened and the contents filtered through a Buchner funnel with medium filter paper using a vacuum aspirator to draw the liquid through the funnel. The wet solids are transferred from the Buchner funnel and placed in a filter press where an additional portion of liquid is pressed from the solids to create a high consistency biomass mixture for enzymatic hydrolysis and further analysis. The dry weight of solid is determined by washing a portion of the solids with water and then oven drying to a constant weight, then amount of biomass removed in the pretreatment cycle given in column e. A small portion of the combined liquid filtrate and pressate (total mass given in column f) is removed for analysis by HPLC, NMR, and elemental analysis via XRF; the remainder is reserved for the next cycle with fresh biomass. A recycle experiment is accomplished by combining the primary filtrate and the pressate liquids with a sufficient quantity of HESA, either recycled from the overheads of the previous run or fresh acid from a 40% wt. stock solution, and water to yield 1000 grams of a 5% wt. acid solution which are returned to a 2 liter C276 Parr reactor where it is mixed with another 120 gram portion of fresh biomass. The pretreatment cycle, venting and recovery, and filtration are repeated a number of times to demonstrate development of significant soluble sugars. The analytical results per cycle are given in Table 1 where the growth in sugars xylose, glucose, and arabinose (as monomer) as well as acetic acid concentration in the filtrate is readily seen (columns f, g, h, and i respectively). The amount of furfural remains very low through all recycles as given in column j. The net increase in xylose and glucose per pass (columns k and l respectively) remains essentially constant with a slight lowering of monomer due to the increased presence of oligomers (not shown).

TABLE 1

Pretreatment with Recycles - 0.25 hour; 120° C., 1500 RPM

| a Example | B Wt. Dry Biomass in run (g) | c g overheaded | d % of starting HESA recovered overhead | e % wt. of solid biomass dissolved | f % wt. Xylose in filtrate | g % wt. glucose in filtrate | h % wt. Arabinose in filtrate | i % wt. Acetic Acid in filtrate | j % wt. Furfural in filtrate | k Net g xylose increase in cycle | l Net g glucose increase in cycle |
|---|---|---|---|---|---|---|---|---|---|---|---|
| 3 | 110.38 | 177.62 | 95.2 | 41.3 | 2.54 | 0.31 | 0.34 | 0.35 | 0.008 | 21.50 | 2.60 |
| 4 | 110.25 | 214.45 | 99 | 40.1 | 4.77 | 0.66 | 0.59 | 0.66 | 0.014 | 21.01 | 3.20 |
| 5 | 109.56 | 179.56 | 98.7 | 45.9 | 6.07 | 0.89 | 0.74 | 0.85 | 0.028 | 20.16 | 3.23 |
| 6 | 110.04 | 117.54 | 92.7 | 43.6 | 6.63 | 1.04 | 0.82 | 0.93 | 0.044 | 20.88 | 3.64 |
| 7 | 110.24 | 110.74 | 89 | 44.1 | 7.35 | 1.21 | 0.95 | 1.04 | 0.059 | 19.27 | 3.53 |

Examples 8-12

Pretreatment Reaction with Recycle; 120° C., 60 Minutes, 1500 rpm Stirring.

This series of recycle experiments was conducted as described for examples 3-7 with results given in table 2. These results show that in the longer time frame of reaction results in a slight increase in sugars, most of the biomass dissolution takes place quickly and α-hydroxysulfonic acid recoveries are generally improved with shorter reaction times.

TABLE 2

Pretreatment with Recycles - 1 hour; 120° C., 1500 rpm

| a Example | B Wt. Dry Biomass in run (g) | c g overheaded | d % of starting HESA recovered overhead | e % wt. of solid biomass dissolved | f % wt. Xylose in filtrate | g % wt. glucose in filtrate | h % wt. Arabinose in filtrate | i % wt. Acetic Acid in filtrate | j % wt. Furfural in filtrate | k Net g xylose increase in cycle | l Net g glucose increase in cycle |
|---|---|---|---|---|---|---|---|---|---|---|---|
| 8  | 109.45 | 164.52 | 92.8 | 42.84 | 2.856 | 0.51  | 0.405 | 0.39  | 0.006 | 23.747 | 4.241 |
| 9  | 110.74 | 131.04 | 88.2 | 43.53 | 4.829 | 0.912 | 0.701 | 0.645 | 0.017 | 23.842 | 4.694 |
| 10 | 110.27 | 189.75 | 89.1 | 36.81 | **** | **** | **** | **** | **** | **** | **** |
| 11 | 109.46 | 108.69 | 90.5 | 39.29 | 7.156 | 1.488 | 1.068 | 0.94  | 0.029 | 21.185 | 4.656 |
| 12 | 110.09 | 182.21 | 94   | 43.05 | 8.892 | 1.783 | 1.251 | 1.063 | 0.033 | 19.877 | 3.603 |

**** Initial filtrate not analyzed.

Examples 13-17

Pretreatment Reaction with Recycle; 120° C., 120 Minutes, 1500 rpm Stirring.

This series of recycle experiments was conducted as described for examples 3-7 with results given in table 3. These results show that in an extended reaction time still results in high yield of sugars with little degradation and low furfural production.

TABLE 3

Pretreatment with Recycles - 2 hour; 120° C., 1500 rpm

| a Example | B Wt. Dry Biomass in run (g) | c g overheaded | d % of starting HESA recovered overhead | e % wt. of solid biomass dissolved | f % wt. Xylose in filtrate | g % wt. glucose in filtrate | h % wt. Arabinose in filtrate | i % wt. Acetic Acid in filtrate | j % wt. Furfural in filtrate | k Net g xylose increase in cycle | l Net g glucose increase in cycle |
|---|---|---|---|---|---|---|---|---|---|---|---|
| 13 | 109.86 | 263.95 | 89.8 | 48.21 | 3.41 | 0.75 | 0.425 | 0.444 | 0.012 | 25.67 | 5.64 |
| 14 | 110.50 | 324.20 | 86.7 | 51.81 | 5.86 | 1.35 | 0.753 | 0.688 | 0.018 | 18.21 | 4.40 |
| 15 | 111.04 | 211.02 | 91.4 | 45.09 | 5.92 | 1.40 | 0.771 | 0.719 | 0.056 | 22.76 | 5.51 |
| 16 | 111.05 | 148.56 | 88.3 | 49.09 | 6.46 | 1.53 | 0.85  | 0.842 | 0.109 | 19.66 | 4.68 |
| 17 | 110.63 | 163.17 | 89.8 | 45.67 | 7.41 | 1.77 | 0.998 | 1.006 | 0.141 | 20.25 | 4.95 |

The existence of the what is thought to be a surfactant species was also analyzed for composition by a combination of techniques including proton NMR, 2d NMR, mass spectroscopy, seperations techniques, to be sulfonated crotonaldehyde and quantified by NMR.

The surfactant species was present in Example 11 in an amount of approximately 0.2 wt %.

Examples 18

Enzymatic Hydrolysis of Biomass Treated with α-hydroxysulfonic Acids

This example demonstrates the ability of the disclosed pretreatment process to produce substrate that is susceptible to enzymatic hydrolysis.

A proportion of the pretreated slurry from Example 11 was used as substrate for enzymatic hydrolysis The extent of hydrolysis was determined by the amount of glucose liberated. Experiments were performed in triplicate.

The enzymatic hydrolysis was performed in 125 mL sealed flasks with 5.0% (unwashed) cellulose (grams of cellulose per 100 mL of slurry) in 50mM Sodium Acetate buffer at pH 5.

The enzyme used was Novozymes Cellic CTec2™, at concentration of 15.0 mg of enzyme (dry weight) per gram of cellulose. The reaction was initiated by mixing the enzyme, preheated to 50° C., with the solid pretreated biomass substrate which had also been preheated to 50° C. The reaction mixture was incubated at 50° C. for upto 96 hours in a shaker incubator (Infors HT Multitron™) at 250 rpm.

In the case of unwashed pretreated samples, the pH of hydrolysis reaction was monitored closely and maintained at a pH range of 4.9 to 5.1 using a solution of 5M sodium hydroxide (NaOH).

Glucose concentrations were determined by high performance liquid chromatography (HPLC) from 0.5 mL aliquots taken from the reaction mixture at appropriate time points during or after the hydrolysis. The aliquots were centrifuged at 13000 g for 1 minute, immediately after removal from the reaction mixture. 100 µL of the resultant supernatant was then diluted in 900 µL of 10 mM sulphuric acid to stop the hydrolysis, followed by HPLC analysis using a Bio-Rad Aminex™ HPX-87P column Percentages of cellulose conversion were calculated from the measured glucose levels and the cellulose content of the original substrate, the latter being determined from the maximum amount of glucose that could be liberated by completely hydrolysing the cellulose.

The results are shown in Table 4 below.

TABLE 4

Enzyme hydrolysis

| Hydrolysis incubation time (hours) | Average % cellulose conversion using 15 mg CTec2/g cellulose | Standard Deviation (n = 2) |
|---|---|---|
| 0  | 0.0  | 0   |
| 24 | 79.5 | 0.2 |
| 48 | 81.5 | 1.1 |
| 72 | 86.3 | 0.9 |
| 96 | 92.2 | 1.2 |

The data demonstrates that the substrate produced by α-hydroxysulfonic acid treatment of lignocellulose is readily hydrolysed by cellulose hydrolysis enzymes. As is typical with enzymatic hydrolysis of lignocellulose, the rate of conversion of cellulose produced by α-hydroxysulfonic acid treatment begins high and then gradually decreases as cellulase activity is diminished over time. Similar trends have been observed with many other pretreated lignocellulose substrates. Furthermore the data indicates near complete conversion of the cellulose to glucose. Taken together, these data-suggests α-hydroxysulfonic acid treatment can ably create cellulase susceptible material.

We claim:

1. A continuous or a semi-continuous process for treating biomass comprising:
   (a) providing a biomass containing polysaccharides;
   (b) contacting the biomass with a solution containing at least one α-hydroxysulfonic acid at a temperature within the range of about 50° C. to about 150° C. and a pressure within the range of 1 barg to about 10 barg to provide a biomass solution, wherein said biomass solution contains in the range of about 1 wt % to about 25 wt % of biomass based on the solution, and thereby hydrolyzing the biomass to produce at least one fermentable sugar containing product;
   (c) removing at least a portion of the α-hydroxysulfonic acid in its component form from the product by heating and/or reducing pressure to produce an acid-removed product containing at least one fermentable sugar;
   (d) separating a high solids/liquid mixture from said acid-removed product to form a wet solids stream containing at least 12 wt % undissolved solids based on wet solids stream, and a bulk liquid stream containing fermentable sugar;
   (e) recycling said removed α-hydroxysulfonic acid to step (b) as components or in its recombined form; and
   (f) recycling at least a portion of the bulk liquid stream to step (b);
   wherein the bulk liquid stream comprise greater than about 2 wt % of the fermentable sugar based on the bulk liquid stream.

2. The process of claim 1 wherein the α-hydroxysulfonic acid is present in an amount of from about 1% wt. to about 55% wt., based on the solution.

3. The process of claim 2 wherein the biomass solution contains greater than about 5 wt % of fermentable sugar.

4. The process of claim 3 wherein the biomass content in the biomass solution is less than about 20 wt %.

5. The process of claim 4 wherein the biomass content in the biomass solution is less than about 15 wt %.

6. The process of claim 5 wherein the biomass content in the biomass solution is about 10 wt % or less.

7. The process of claim 1 wherein the separation of step (d) is by centrifugal force.

8. The process of claim 1 wherein the separation of step (d) is by filtration.

9. The process of claim 1 wherein the separation of step (d) is by decantation.

10. The process of claim 1 further separating a pentose-containing stream from the liquid stream.

11. The process of claim 1 wherein the hexose content of the wet solid stream is greater than about 0.5 wt % based on the wet solid stream.

12. The process of claim 11 wherein the wet solid stream contains less than 0.5 wt % furfural.

13. The process of claim 12 wherein the wet solid stream contains less than 0.2 wt % furfural.

14. The process of claim 1 wherein the α-hydroxysulfonic acid is produced from (a) a carbonyl compound or a precursor to a carbonyl compound with (b) sulfur dioxide or a precursor to sulfur dioxide and (c) water.

15. The process of claim 1 wherein the α-hydroxysulfonic acid is in-situ generated.

16. The process of claim 2 wherein the biomass is contacted with the α-hydroxysulfonic acid at a temperature of 120° C. or less.

17. The process of claim 2 wherein the α-hydroxysulfonic acid is produced from (a) a carbonyl compound or a precursor to a carbonyl compound with (b) sulfur dioxide or a precursor to sulfur dioxide and (c) water.

18. The process of claim 2 wherein the α-hydroxysulfonic acid is in-situ generated.

19. The process of claim 1 wherein the at least one fermentable sugar comprises a hexose.

20. The process of claim 1 wherein in step (b) at least one pentose and at least one hexose is produced.

21. The process of claim 1 further comprising (g) hydrolyzing the liquid/solid mixture thereby producing a sugar stream.

22. The process The process of claim 21 further comprising (h) fermenting the sugar stream thereby producing fermented products.

23. The process of claim 2 further comprising hydrolyzing and fermenting the stream containing fermentable sugar thereby producing fermented products.

24. The process of claim 1 wherein the α-hydroxysulfonic acid is present in an amount of from about 1% wt. to about 40% wt., based on the solution.

25. The process of claim 1 wherein in step (c) the acid-removed product is substantially free of the α-hydroxysulfonic acid.

26. The process of claim 25 wherein in step (c) no more than about 2 wt % of alpha-hydroxysulfonic acid is present in the acid-removed product.

* * * * *